United States Patent [19]

Lahoda

[11] Patent Number: 5,323,662
[45] Date of Patent: Jun. 28, 1994

[54] BENCH SCALE PROCESS AND APPARATUS FOR DETERMINING OPERATING PARAMETERS OF A THERMAL DESORPTION PROCESS

[75] Inventor: Edward J. Lahoda, Edgewood Borough, Pa.

[73] Assignee: Westinghouse Electric Corporation, Pittsburgh, Pa.

[21] Appl. No.: 933,170

[22] Filed: Aug. 21, 1992

[51] Int. Cl.$^5$ .............................................. F26B 21/06
[52] U.S. Cl. .......................................................... 73/866
[58] Field of Search ...................... 73/866; 374/43, 44, 374/141, 142, 137; 210/773, 774, 775; 34/79

[56] References Cited

U.S. PATENT DOCUMENTS

| | | |
|---|---|---|
| 3,432,397 | 3/1969 | Berg . |
| 3,954,069 | 5/1976 | Loken . |
| 4,050,900 | 9/1977 | Hobbs et al. . |
| 4,059,982 | 11/1977 | Bowman ............................. 374/44 |
| 4,738,206 | 4/1988 | Noland . |
| 4,756,092 | 7/1988 | Anderson et al. . |
| 4,782,625 | 11/1988 | Gerken et al. . |
| 4,864,942 | 9/1989 | Fochtman et al. . |
| 4,977,839 | 12/1990 | Fochtman et al. . |
| 5,230,167 | 7/1993 | Lahoda ................................ 34/79 |

FOREIGN PATENT DOCUMENTS 1617368 12/1990 U.S.S.R. .............................. 374/142

OTHER PUBLICATIONS

*Process Technology and Flowsheets,* McGraw-Hill, 1979, pp. 225–226.
*Contaminated Land Reclamation and Treatment,* Michael A. Smith ed., Plenum Press, 1985, pp. 37–90, "On-Site Processing of Contaminated Soil" by W. H. Rulkens.
EPA Applications Anaylsis Report, *Shirco Infrared Incineration System,* Jun. 1989, pp. 39–42.

*Primary Examiner*—Robert Raevis
*Attorney, Agent, or Firm*—Daniel P. Cillo

[57] ABSTRACT

A bench scale process and apparatus for determining the operating parameters, such as maximum temperature and residence time, required to remove a particular contaminant at a particular depth during a full-scale thermal desorption process, includes measuring a temperature of a representative contaminated soil sample at a particular depth as a function of residence time during a bench scale thermal desorption process. The method also includes measuring the contaminant level of the soil sample after the bench scale process to determine the required temperatures and residence times to substantially remove the contaminants from the soil. The apparatus includes a container for housing the soil sample, at least one partition positioned between adjacent layers of the soil sample and at least one thermocouple positioned within each layer of the soil sample. In determining the operating parameters, the heat flux, absorptivity, thermal diffusivity and thermal conductivity may be determined during the bench scale process and utilized to predict the operating parameters of the full scale process.

20 Claims, 4 Drawing Sheets

BENCH SCALE PROCESS AND APPARATUS FOR DETERMINING OPERATING PARAMETERS OF A THERMAL DESORPTION PROCESS

BACKGROUND OF THE INVENTION

This invention relates to an apparatus and method for removing volatile and semi-volatile contaminants from solid materials by thermal desorption and, more particularly, to a bench scale apparatus and method for evaluating the effective interaction between soils and contaminants in order to determine the operating parameter requirements and applicability of thermal desorption for removal of organics and metals from soils.

The contamination of soils, sludges, ashes, and other solids by organics and metals is a significant environmental problem. Due to the large volumes involved and the expensive disposal costs for these solids, there is a need to reduce the volume of waste requiring disposal.

The contaminated soil may be treated by separation of the contaminants from the soil, such as by thermal desorption. During thermal desorption, the contaminants are heated under oxygen concentrations and residence time to a temperature effective to avoid decomposition of the contaminants, thereby enabling the separation of the volatilized contaminants from the soil.

As examples of thermal treatment of soil, the contaminated soil may be conveyed through a chamber by a screw conveyor with internally heated flights, placed within a rotary kiln, placed within a rotating cylinder having plural flights, or conveyed through a chamber on a conveyor belt.

An example of a thermal desorption unit which utilizes a conveyor belt is disclosed in U.S. Pat. No. 5,230,167 (Lahoda et al.), which is herein incorporated by reference. The method for removing contaminants from contaminated soil includes moving the contaminated material positioned on a belt conveyor through a chamber from an inlet end of the chamber to a discharge end of the chamber under oxygen concentration conditions, temperature conditions, and residence times effective to avoid incineration, combustion or oxidation of the contaminated material and the contaminants.

The contaminated material positioned on the belt conveyor in the chamber is heated, such as by a plurality of infrared heaters, either electric or gas fired, microwave, or other methods, positioned within or near the chamber, as the contaminated material moves through the chamber, to a temperature effective for volatilizing the contaminants and for producing a processed material that is substantially decontaminated.

A transport gas, such as steam, nitrogen, or carbon dioxide, is passed through the chamber, either cocurrent or countercurrent, to the movement of the contaminated material on the belt conveyor for transporting the volatile contaminants from the chamber. The volatilized contaminants are then discharged from the chamber to be further processed. The volatilized contaminants are condensed, separating the volatilized contaminants from the gas stream and producing a contaminated liquid condensate, which may be further processed.

The method may also include drying or wetting the contaminated material prior to entry of the contaminated material into the chamber, preventing air from entering the chamber, and scrubbing the condensed gas stream. To minimize the temperature gradient in the soil bed and to eliminate hot spots, the soil may be turned over several times using motorized rakes, chains or other means during the heating cycle.

To qualify the thermal desorption process, the applicability of thermal desorption to remove contaminants from the solids found at any particular site needs to be verified. To determine if the thermal desorption process is applicable to remove contaminants, the cost of operation, which requires the specification of operating parameters, such as residence time, power input, maximum required soil temperature, and effect of soil depth on the conveyor belt, needs to be determined.

Therefore, what is needed is a thermal desorption evaluation apparatus and procedure which may be performed on a sample of contaminated material for providing the operating parameters of a full scale process for particular contaminants and types of contaminated materials.

SUMMARY OF THE INVENTION

A method for determining operating parameters for a thermal desorption process which removes contaminants from contaminated soil includes obtaining a representative contaminated soil sample from a site containing the contaminated soil. A temperature of the soil sample is measured at particular depths of the soil sample as a function of the residence time by passing at least a portion of the soil sample through a bench scale thermal desorption process. A thermal conductivity and absorptivity for the soil sample is determined by using the temperature as a function of the residence time and the depth obtained through the bench scale thermal desorption process. Using the thermal conductivity and absorptivity, the operating parameters of the full scale process may be determined to achieve the maximum temperature and residence time required for removal of a particular contaminant during the thermal desorption process.

Also, the method may further include the steps of analyzing the soil sample to identify particular contaminants contained within the soil sample and measuring the contaminant level of the soil sample after the bench scale process for determining the maximum temperature and residence time required to substantially remove the contaminants from the soil sample.

A bench scale apparatus includes a container having a plurality of walls and an open end for housing a soil sample, at least one partition positioned between adjacent layers of the soil sample within the container, and at least one thermocouple positioned within each layer of the soil sample for measuring a temperature of the soil sample at particular depths within the container. The apparatus may also include a cover positioned over the open end and insulation positioned within the container.

BRIEF DESCRIPTION OF THE DRAWINGS

While the specification concludes with claims particularly pointing out and distinctly claiming the subject matter of the invention, it is believed the invention will be better understood from the following description, taken in conjunction with the accompanying drawings, wherein:

DESCRIPTION OF THE PREFERRED EMBODIMENT

The invention described herein provides an apparatus and method for determining the operating parameters of a thermal desorption process for removing organics and metals from the soil.

Figure 1:
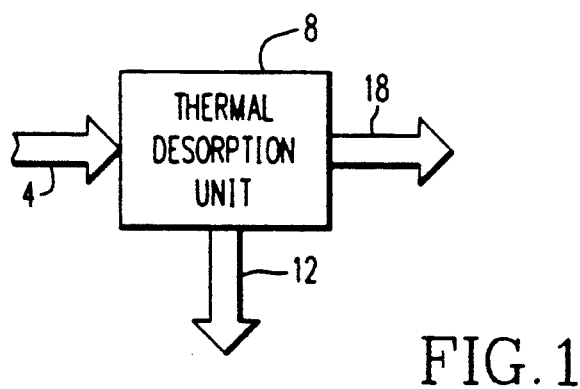
FIG. 1 is a schematic representation of a typical thermal desorption process.

Referring to FIG. 1, a simplified schematic of a typical thermal desorption process is illustrated, in which contaminated soil, generally 4, is transported through a thermal desorption process, generally 8. The soil is heated until substantially all of the contaminants have been vaporized. The contaminants may be removed from the thermal desorption process 8 through stream 12 and the substantially clean soil may be removed through stream 18. The contaminants may be further processed. The clean soil that is recovered may be returned to the site. The process illustrated in FIG. 1 reduces the volume of contaminated material and therefore the cost of destroying the contaminated material.

Figure 2:
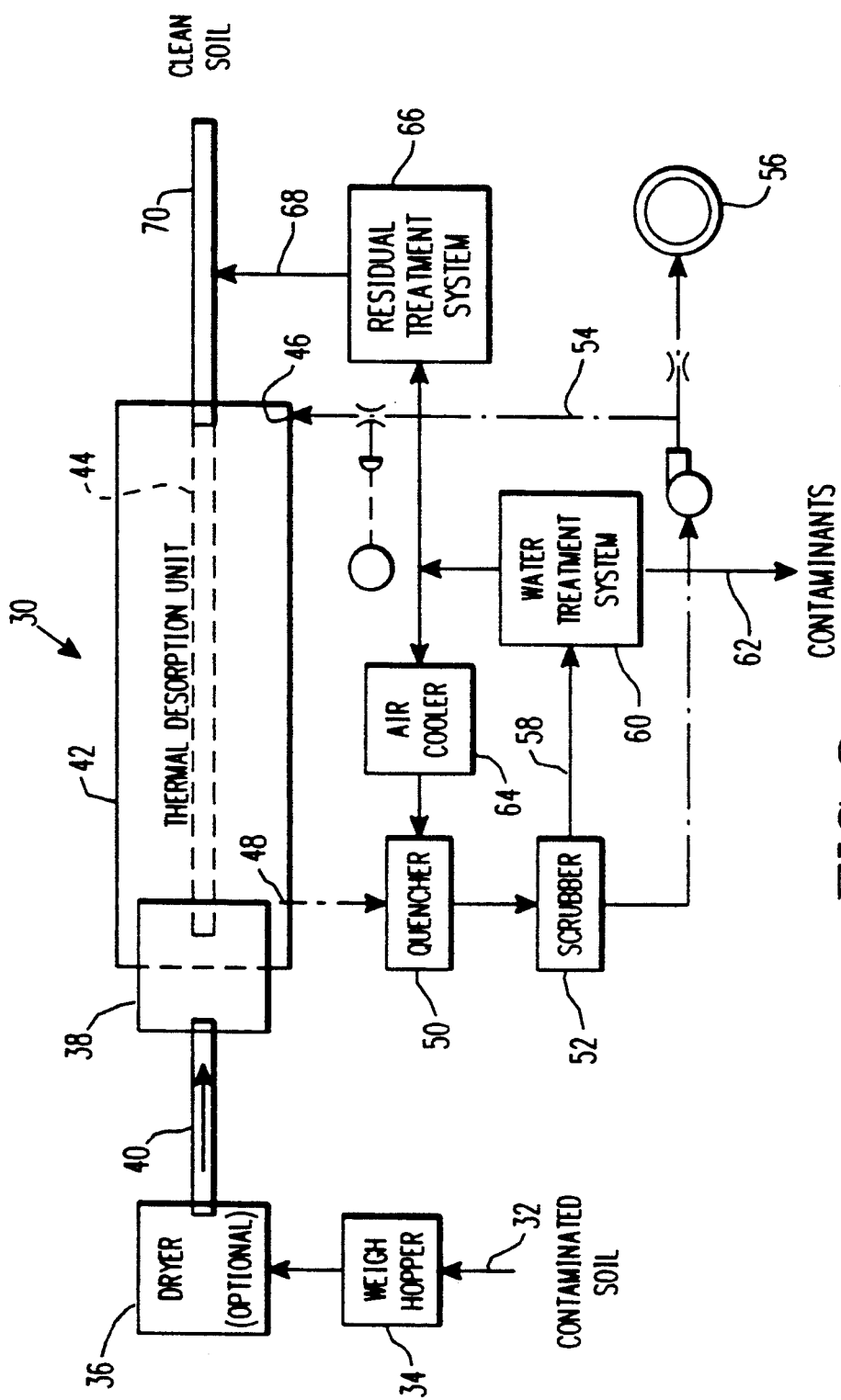
FIG. 2 is a more detailed schematic representation of a typical thermal desorption process.

Referring to FIG. 2, a particular embodiment of a thermal desorption process is illustrated. This process is described in U.S. Pat. No. 5,230,167 (Lahoda et al.) patent application Ser. No. 07/785,397, commonly owned by the assignee of the present invention. The excavated soil 4 is processed in a thermal desorption unit 30. The contaminated material is passed through stream 32 into a weigh hopper 34, which maintains a constant feed rate of contaminated material to the thermal desorption unit 30.

Water may be evaporated from the contaminated material in a dryer 36 prior to entering the thermal desorption unit 30 or the contaminated material may be dried within the thermal desorption unit 30 by heaters positioned with the unit 30.

After exiting from the dryer 36, the contaminated soil is conveyed to a feed hopper 38 on a feed conveyor 40, which is substantially enclosed. The contaminated material falls through an opening in the top of a chamber 42 of the thermal desorption unit 30 and onto a belt conveyor 44 positioned within the chamber 42. To minimize a temperature gradient in the soil bed and to eliminate hot spots, the soil is turned over using motorized rakes, chains or other devices several times during the heating cycle.

The contaminated material is heated by the heaters, such as infrared heaters, as the material moves through the chamber 42 while positioned on the belt conveyor 44. The material will be heated to a temperature effective to volatilize the contaminants from the soil, such as within the range of 100° C. to 800° C. The temperature, oxygen concentrations, and residence time will be maintained at effective levels for avoiding incineration of the contaminants.

A transport gas may be is passed into the chamber 42 through a gas inlet duct 46. The gas transports the volatilized contaminants countercurrent or cocurrent to the flow of the contaminated material on the belt conveyor 44 above the belt conveyor 44. The gas and the volatilized contaminants exit the chamber 42 through a gas outlet duct 48.

The vapor product off-gas, which may include the transport gas and the volatilized contaminants, passes to a quencher 50, which provides a cold water shower for lowering the temperature of the gas to below its saturation point to condense the vapor product off-gas. From the quencher 50, the gas stream passes to a scrubber 52, which uses the water droplet contact for removing the remaining solids and contaminants from the gas stream. A clean gas stream and a contaminated liquid condensate will exit from the scrubber 52.

A portion of the cleaned gas stream may pass through stream 54 into the chamber 42 for recycling the gas. The remainder of the cleaned gas stream passes into a gas cleaning system 56 for an additional cleaning step prior to discharge into the atmosphere.

The contaminated liquid condensate passes through stream 58 into the water treatment system 60 for removal of an organic or inorganic contaminant sludge using gravitational settlement, flocculation, or carbon absorption. The contaminated sludge and absorbed contaminants are passed through stream 62 for removal from the site for further processing.

A portion of the decontaminated water passes from the water treatment system 60 into the air cooler 64 and then, into the quencher 50 for recycling the water. A portion of the decontaminated water is passed into a residual treatment system 66 for removing residual organics and metals, and then passed through stream 68 for quenching the clean soil exiting the chamber 42.

Clean soil drops from an end of the belt conveyor 44 onto a conveyor 70, exiting the thermal desorption unit 30. After quenching the clean soil discharged from the chamber 42 to lower the temperature of the soil, the soil is returned to the environment.

To efficiently operate a full scale thermal desorption process, the operating parameters, such as the maximum solids temperature, oxygen concentrations, and residence time can be determined by utilizing a bench scale process.

Figure 3:
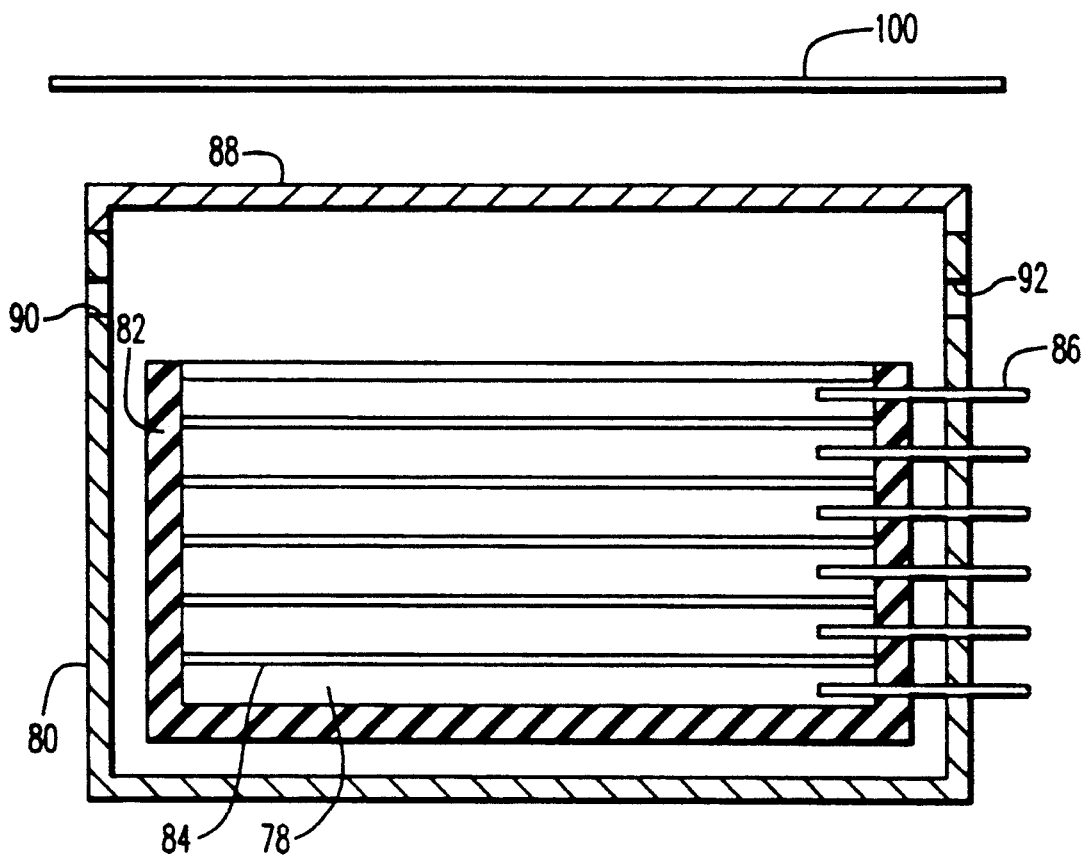
FIG. 3 is a schematic representation of a bench scale thermal desorption apparatus.

Referring to FIG. 3, in practicing the bench scale process, a representative soil sample 78 is removed from the contaminated soil site. The representative soil sample is placed within a container 80. The container 80 may be constructed of a metal, such as 304 stainless steel or other suitable material. Insulation 82 may be positioned within the container 80 for reducing the conduction of heat into the soil from the sides of the container 80 allowing the soil within the container 80 to be heated mainly from the top of the container 80.

A partition, such as a screen 84, is positioned between adjacent layers of soil within the container 80. The screen 84 may be constructed of a metal, such as nickel. The screen 84 provides a means of demarcating each soil layer and allows for the retrieval and analysis of each layer of soil for residual contaminant levels after the bench scale test is conducted.

A thermocouple 86 is positioned approximately in the center of each layer of soil for measuring the temperature of the soil at specific depths. The thermocouples 86 may be connected to a processor (not shown) for logging and monitoring the temperature data.

A cover 88, which may be constructed from a metal, such as stainless steel, is placed over the top of the container 80 to provide a gas tight seal. A gasket may be positioned between the cover 88 and the top of the container 80 for providing the seal. The cover 88 may have a thermocouple attached, such as by welding, to an underside of the cover 88 to monitor the temperature of the cover 88.

The container 80 has an inlet gas port 90 and an outlet gas port 92, which may be machined into the walls of the container 80 or the cover 88. The transport gas is passed into the container 80 through the inlet gas port 90, across the air space above the soil, and through the outlet gas port 92. The volatilized contaminants are removed from the container 80 with the transport gas.

Figure 4:
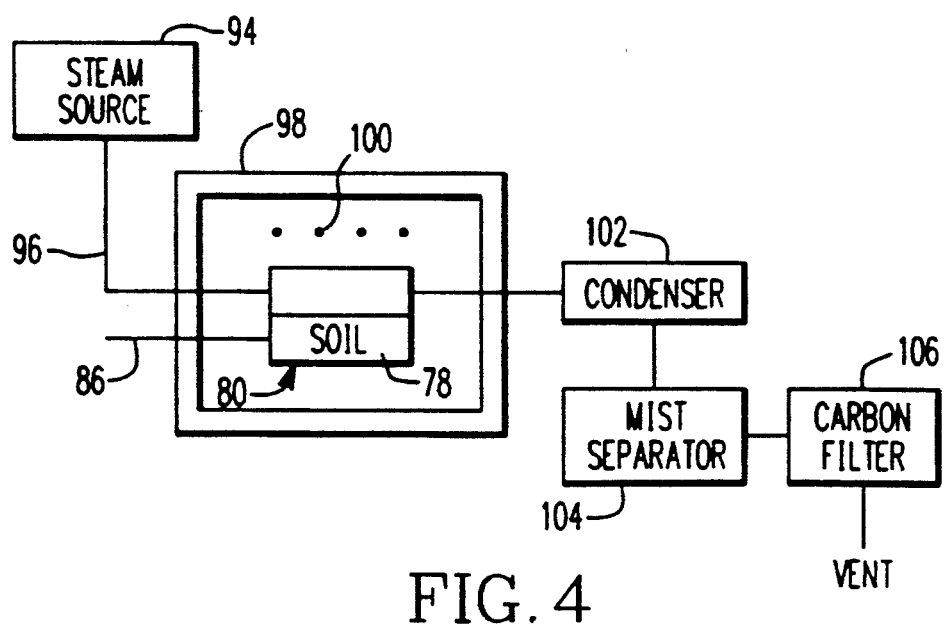
FIG. 4 is a schematic representation of bench scale thermal desorption process.

Referring to FIGS. 3 and 4, steam may be used as the transport gas to minimize the gas cleaning requirements. A steam source 94 positioned adjacent the container 80 provides the steam to the container 80 through a steam line 96. The steam line 96 may be wrapped with heating tape to prevent the steam from condensing prior to entry into the container 80. The steam is not passed into the container 80 until the soil surface temperature is at least approximately 100° C. to prevent the steam from condensing on the soil surface.

The container 80 housing the representative soil sample is placed within a furnace 98. Within the furnace 98 is positioned a plurality of heaters 100, such as silicon carbide heating rods or infrared heaters. The thermocouples 86, steam lines 96 and connections of the heating rods 100 to a power supply pass through apertures in a wall of the furnace 98.

The steam including the volatilized contaminants discharged from the container 80 may be passed through at least one condenser 102. Any noncondensing gases discharged from the condensers 102 may be directed through a mist separator 104. The gas may then be passed through an activated carbon filter 106 prior to discharge into the atmosphere. Other gas treatment systems may be used as required.

Figure 5:
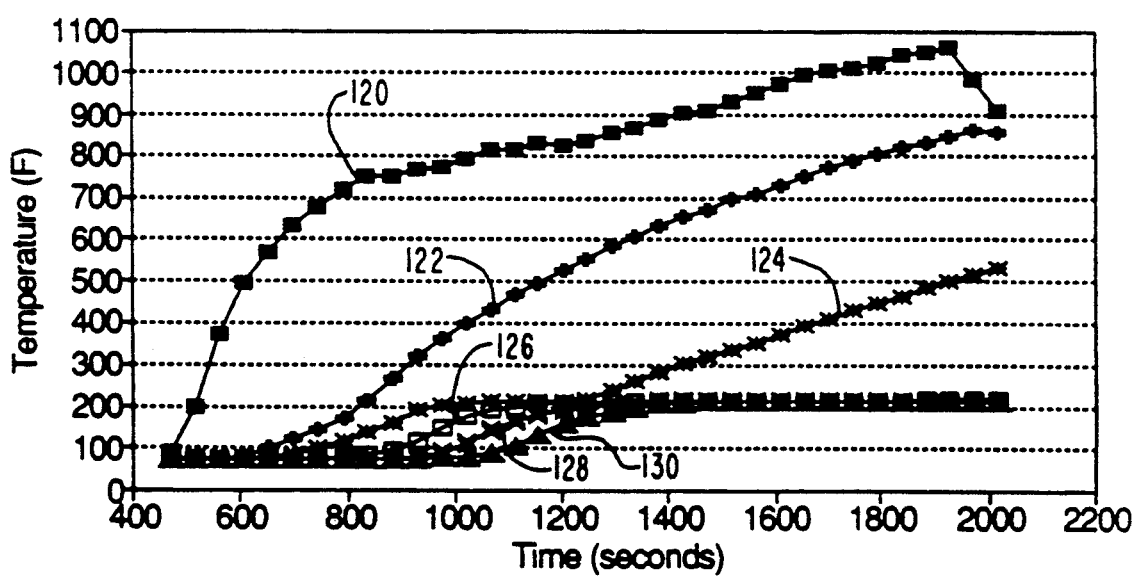
FIG. 5 is a graph of temperature versus residence time for particular soil depths.

Several samples of soil may be processed through the bench scale apparatus. Readings may be obtained from the plurality of thermocouples 86 positioned at various depths of soil as a function of residence time. The temperature at a particular depth may be plotted versus the residence time at that particular depth, such as illustrated in FIG. 5. Referring to FIG. 5, line 120 illustrates the temperature of the cover 88 of the container 80. Line 122 illustrates the temperature of the surface of the soil sample 78. Line 124 illustrates the temperature of the soil approximately 0.5 inches (1.3 cm) below the surface of the soil sample 78. Line 126 illustrates the temperature of the soil approximately 1.0 inch (2.5 cm) below the surface of the soil sample 78. Line 128 illustrates the temperature of the soil approximately 1.5 inches (3.8 cm) below the surface of the soil sample 78 and line 130 illustrates the temperature of the soil approximately 2.0 inches (5 cm) below the surface of the soil sample 78.

Figure 6:
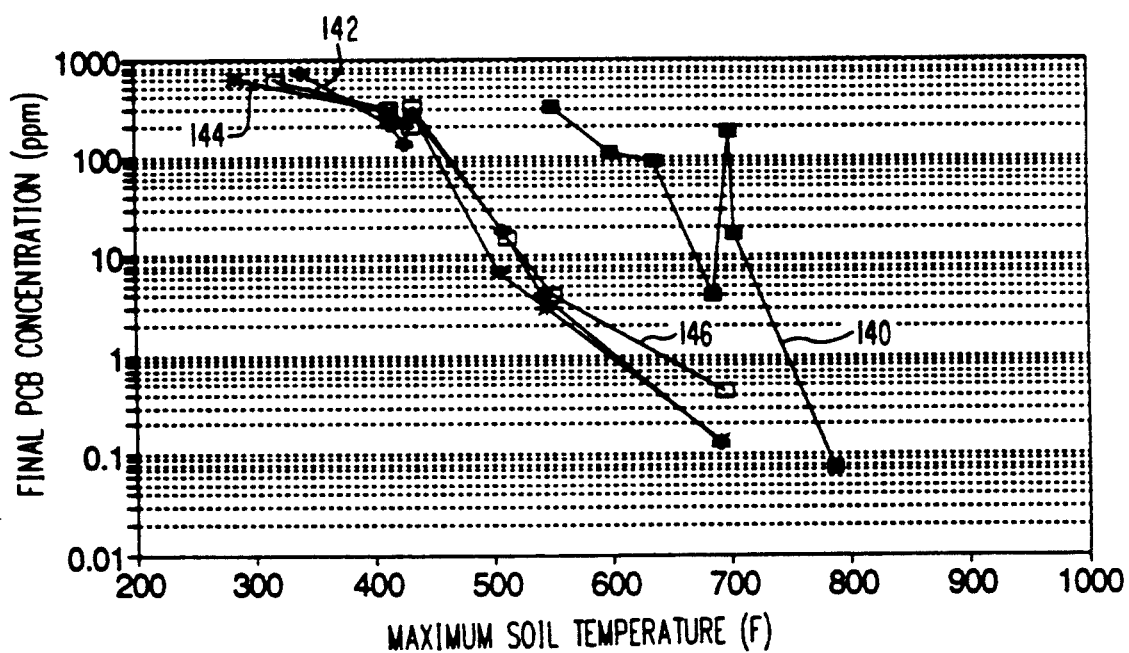
FIG. 6 is a graph of contaminant concentrations versus maximum temperature for particular soil depths in the bench scale thermal desorption apparatus.

The contaminant level of each layer of soil can be analyzed to determine the maximum temperature and residence time required to substantially remove the contaminants from the soil. One graph illustrating contaminant concentration versus temperature is shown in FIG. 6. Referring to FIG. 6, line 140 illustrates the contaminant level of the soil approximately 0.5 inches (1.3 cm) below the surface of the soil sample 78. Line 142 illustrates the contaminant level of the soil approximately 1.0 inch (2.5 cm) below the surface of the soil sample 78. Line 144 illustrates the contaminant level of the soil approximately 1.5 inches (3.8 cm) below the surface of the soil sample 78. Line 146 illustrates the contaminant level of the soil approximately 2.0 inches (5 cm) below the surface of the soil sample 78.

The operating parameters for the thermal desorption unit are determined by using the data from the bench scale apparatus, including container 80, in combination with a mathematical model. The mathematical model utilizes a heat transfer mathematical equation, such as, for example, the following equation developed by Carslow and Jaeger, *Conduction of Heat in Solids*, 2nd edition, $$T - T_o = 2*F_o/k*((M*t/3.14)^{1/2}*\exp(-x^2/4/m/t) - x/2*\mathrm{erfc}(x/2/(M*t)^{1/2})) \quad (1)$$

or $$T - T_o = 2*F_o/M/d/C_p*((M*t/3.14)^{1/2}*\exp(-x^2/4/t/M) - x/2*\mathrm{erfc}(x/2/(M*t)^{1/2})$$

where $$M = k/d/C_p \quad (2)$$

where
T = temperature at time = t at depth = x
$T_o$ = initial temperature,
$F_o$ = heat flux,
k = thermal conductivity,
M = thermal diffusivity,
t = residence time,
x = depth,
d = density, and
$C_p$ = heat capacity.

This mathematical model for the thermal desorption process assumes a constant heat flux, $F_o$, onto the surface of the soil bed. This assumption is valid due to the large temperature difference between the heating rods and the surface temperatures of the soil.

An indefinite depth of soil is assumed because of the relatively low thermal conductivity and the thickness of the bed, which tends to keep the side of the bed on the belt conveyor at the initial bed temperature. For this assumption to be valid, the bed depth must be more than the thermal penetration depth, z, where:

$$z = 4*(M*t)^{\frac{1}{2}}$$

If the thermal penetration depth is greater than the bed depth, the bed temperature will be under estimated, which will lead to a conservative calculation for the residence time required in the thermal desorption unit.

Also, assumed are constant bed properties throughout the depth, x, of the bed during the applicable time period, and a constant initial temperature, $T_o$, which are justified assumptions due to the mixing of the soil at regular intervals, which eliminates the temperature gradient.

Based on the mathematical equation (1), for a constant flux of heat at the surface of a semi-infinite solid, the important variables are the heat capacity, Cp, of the bed, the effective thermal conductivity, k, of the bed (assumed to be the solids fraction, f, times the pure solids thermal conductivity), and the density of the soil, d (assumed to be the solids fraction, f, times the pure solid density).

The density (gm/cc) of the soil bed is determined by weighing a portion of the soil, and then measuring the volume of the portion of soil, such as in a graduated cylinder. This density is referred to as bulk density. The absolute density of the soil may be determined by referring to a reference book.

To determine the solids fraction, f, the absolute density is divided by the bulk density. The heat capacity, Cp, can be obtained from reference literature, for example, 0.22 cal/gm/° C. for dry soils.

Testing is aimed at determining the thermal conductivity, k, and the absorptivity, a. By determining the effective thermal conductivity, k, and the absorptivity, a, the temperature profile of the soil can be predicted for any set of operating parameters. In addition, the effects of soil bed depth, maximum soil bed temperature and residence time on the final soil contaminant level can be determined and a regression model developed. The maximum solids temperature and residence time will be significant factors.

The temperature profile as a function of time and distance into the bed of soil are measured during the bench scale thermal desorption process, as the representative soil sample is monitored within the container 80.

The initial step in using the mathematical model is to calculate the heat flux, $F_o$, in cal/cm²/sec, which can be determined by an equation, such as:

$$F_o = m_i/A * (C_p/\Delta T_i/\Delta t_i + w*540/\Delta T_e) \quad (3)$$

where
$m_i$ = mass of each bed layer in grams,
$\Delta T_i$ = temperature difference through the bed,
$\Delta t_i$ = time difference of temperature difference,
A = area of bed,
$\Delta T_e$ = time to evaporate water (in second zone), and
w = weight percent water in soil.

After the heat flux, $F_o$, is determined by substituting the data obtained from the bench scale process into equation (3), the absorptivity, a, of the soil is calculated using an equation, such as:

$$a = (eT_L^4 - F_o/\sigma)/T_s^4 \quad (4)$$

which is derived from:

$$F_o = \sigma(eT_L^4 - aT_s^4) \quad (4a)$$

where
$F_o$ = heat flux (as calculated from Eq. (3))
e = emissivity of soil container cover,
$\sigma$ = Stephan-Boltzman constant = $1.355 \times 10^{-12}$ cal/sec/cm²° K$^{-4}$,
$T_L$ = temperature of soil container lid,
$T_s$ = temperature of soil surface.

Substituting the heat flux, $F_o$, as calculated from equation (3) and the data obtained from the bench scale process into equation (1), the thermal diffusivity, M, can be solved for. Using equation (2) and the value obtained from equation (1) for M, the thermal conductivity, k, can be determined.

As an alternative to using equation (2) and the value of M obtained from equation (1), the thermal conductivity, k, can be determined by the differentiation of equation (1) by time, t, which yields:

$$\partial T/dt = 2*F_o/k((M/\pi)^{1/2}*1/2*t^{-1/2}\exp(-x^2/4Mt) + (M/\pi)^{1/2}t^{1/2}x^2/4Mt^2\exp(-x^2/4Mt) - x^2/2\pi^{1/2}(\exp(x^2/4Mt))x/2M^{1/2}(t^{1/2})1/T^{3/2})$$
$$= 2F_o/k(M/4\pi)^{1/2}1/t^{1/2}\exp(-x^2/4Mt)$$

During the bench scale process, the change in temperature with time (dT/dt) for each thermocouple is measured. Substituting the heat flux, $F_o$, as calculated from equation (3), and the values obtained from the bench scale process for dT/dt into equation (5), the thermal diffusivity, M, can be determined. Using equation (2) and the value obtained from equation (5) for M, the thermal conductivity, k, can be determined.

Substituting the thermal conductivity, k, into equation (2) in combination with equation (1), equation (1) can be used to predict maximum temperature and residence time for particular contaminants at particular depths for the full scale thermal desorption process. For example, if the contaminant is PCB and the thickness of the soil in the thermal desorption unit is 2 inches, then the calculated thermal conductivity, k, the depth of 2 inches, and the temperature, $T_f$, required to volatilize PCB's are substituted into equations (1) and (2) to solve for residence time, $t_r$.

The final contaminant levels attained in the soil are analyzed along with the operating parameters used in the bench scale tests. An equation such as the following (from data in FIG. 6) may be developed by regression analysis from the laboratory data:

$$Lf = Li*\exp(38.813 - 0.0448*Tf - 0.0006094*Tf*tr) \quad (6)$$

where
Lf = final contaminant level
Li = initial contaminant level
Tf = maximum temperature
tr = residence time Depth does not enter into equation (6) because diffusion effects are negligible for thin beds of material, such as less than 2 inches, and the degree of contaminant removal is determined by the maximum temperature attained by the soil.

The operating parameters are then used to estimate the throughput of the thermal desorption unit. To determine the throughput, the heating capacity of the thermal desorption unit is determined at several power levels. Calculations using the absorptivity of the soil and equation (4a) will determine the rod radiant heat capacity at a specific rod operating temperature and soil temperature. A net radiant energy on the bed surface is determined by multiplying the rod radiant heat capacity by the ratio of rod to heated bed area. This figure may be used to determine the heating capacity of the full scale unit. The amount of absorbed energy is calculated using equation (1). These calculations balance the amount of energy transferred by conductivity into the soil on the belt conveyor versus the energy transferred by radiation from the heaters to the soil surface. When these energies are equal, the capacity of the full scale unit has been determined.

Before capacity calculations are carried out, instead of assuming that the heat capacity is that of the dry solid, for example, $C_p$, equals 0.22 cal/gm/° C., a $C_p$ reflecting the presence of water in the soil may be generated. It is assumed that the heat of vaporization (540 cal/gm) is taken up over the entire soil heatup range, which may be, for example, approximately 70° F. to 850° F. (20° C. to 450° C.). This is a conservative estimate because water will evaporate from the soil at a lower temperature, i.e. 212° F. (100° C.), which will result in better heat transfer between the heated rods and the soil. For example, for a soil containing x% (by weight) water and the heat up range being approximately 70° F. to 850° F. (20° C. to 450° C.), the effective $C_p$ may be determined by the following equation:

$$C_p = 540 \text{ cal/gm}/(850° \text{ F.} - 70° \text{ F.}) \cdot x \cdot 1.8° \text{ F./° C.} + (1-x) \cdot 0.22 \text{ cal/gm/° C.} \quad (7)$$

The required maximum temperatures and residence times are calculated for achieving various contaminants levels for specific contaminants. The heat transfer calculations may be carried out for specific depths of soil. The temperature of the solids can be determined for a given heat flux, residence time, and solid depth. To achieve a given concentration of the contaminant of interest, the required temperature may be determined by considering the concentration of the contaminant as a function of depth and temperature. The required residence time as a function of soil depth can be determined for the infrared thermal desorption unit based on achieving the required temperature at the bottom of the solids bed at the end of the desorber conveyor belt.

It should be understood that the foregoing detailed description is not limited to the determination of the soil parameters (required maximum temperature, effective conductivity and effective absorptivity) of an infrared-rod belt conveyor thermal desorption system. The same technique can be applied to other heating applications, such as rotary kiln-type heaters and screw heaters.

It should be understood that the foregoing detailed description is not limited to the utilization of the equations and/or modeling techniques described hereinabove. The same methodology may use other equations and/or modeling techniques to achieve the same analysis. The determination of the soil parameters using a bench scale process can be used with other similar equations to size various soil heating processes.

EXAMPLE

As an example, approximately 200 grams of contaminated soil was placed within a container. The soil sample had bed dimensions of approximately 2.5 inch (6.3 cm)×2.5 inch (6.3 cm)×2 inch (5.1 cm) deep. The thermocouples were positioned at 0.5 inch (1.3 cm) intervals starting with a thermocouple positioned at the soil bed surface. The volume of the soil in the container was approximately 200 cm³ and about 300 grams of soil was loaded into the container for each test providing a bed density of 1.46 g/cm³. Temperature readings were logged every 30 seconds from the time that the furnace was turned on.

The soil was analyzed prior to the bench scale process and was found to contain approximately 620 ppm of Aroclor 1260, a form of polychlorinated biphenyl. The as received moisture content of the soil was determined to be 9% by weight and the bulk density of the soil was about 1.4 g/cc.

Table 1 illustrates the resulting data obtained from the bench scale thermal desorption process.

TABLE 1

ANALYTICAL RESULTS OF THERMAL DESORPTION TEST

| Test | Surface Temp Hold Time | Aroclor Concentration (ppm) per 1 cm thick layer | | | | |
|---|---|---|---|---|---|---|
| | | 1/5 (surface) | 2/5 | 3/5 | 4/5 | 5/5 (bottom) |
| 1 | 850° F. 0 min | 82 | 310 | 720 | 620 | 580 |
| 2 | 950° F. 0 min | 190 | 180 | 280 | 280 | 320 |
| 3 | 850° F. 0 min | 100 | 109 | 211 | 290 | 298 |
| 4 | 950° F. 0 min | 27 | 16 | 17 | 7 | 15 |
| 5 | 850° F. 5 min | 84 | 90 | 134 | 223 | 202 |
| 6 | 850° F. 10 min | 7 | 4 | 4 | 3 | 4 |
| 7 | 950° F. 5 min | 0.08 | 0.29 | 0.38 | 0.69 | 0.54 |
| 8 | 950° F. 10 min | 0.04 | 0.09 | 0.13 | 0.14 | 0.43 |

Using equation (3), where $m_i = 32$ g, $C_p = 0.22$ cal/° C./g, $A = 40$ cm², and $w = 9$ w/o for the bench scale test, reduces this equation to:

$$F_o = 0.19 \, \Delta t(\Delta T_1) + 42/\Delta T_e \quad (8)$$

Substituting $F_o$ as calculated from equation (8), $e = 0.7$ for 304 stainless steel, and $\sigma = 1.355 \times 10^{-12}$ cal/sec/cm²° K⁻⁴ into equation (4) yields:

$$a = (0.7 \, T_L^4 - F_o/1.355 \times 10^{-12})/T_S^4$$

Substituting the data shown in FIG. 5 into equation (4) yields an effective absorptivity of about 0.6.

Based on these parameters, a value of M can be backed out of the model equation (1). Substituting $d = 1.46$ g/cm³ (measured from soil sample) and $C_p = 0.22$ (literature) into equation (2), yields:

$$M = k/0.31$$

Substituting $M = k/0.31$ and $\pi$ into equation (5) yields:

$$dT/dt = 0564 \, F_o/(kt)^{\frac{1}{2}} \cdot \exp(-x^2/(12.9 \, kt)) \quad (9)$$

After substituting the measured change in temperature with time (dT/dt), the data shown in FIG. 5, into equation (9), equation (9) was then solved for the effective thermal conductivity, k, of the soil, about 0.00017 cal/gm° C.

This value of k is substituted into equations (1) and (2) to solve for temperature at particular times and depths.

This data was used to estimate the throughput of the infrared belt desorber. Calculations using the absorptivity of the soil and equation (4a) were carried out. These indicated that for a rod operating temperature of 1600° C. and a maximum soil temperature of 510° C., a total of 307 watts/in² could be transferred. Since this exceeded the capacity of the heating rods, the rod capacity of 70 watts/in² was used in further calculations. The rod radiant heat capacity was multiplied by the ratio of the rod/heated bed area to obtain a net radiant energy on the bed surface of 1.75 cal/sec/cm². This figure was used to determine the heating capacity of the full scale unit. Since this was equivalent to a total of 2.4 MW and the current power supply only delivered 1 MW of power, a value of 1.75/2.4 or 0.73 cal/sec/cm² was used for the pilot scale unit. The capacity calculations for the pilot scale unit and the full scale unit are presented in Table 2.

TABLE 2

CAPACITY CALCULATIONS MAXIMUM TEMPERATURE AND RESIDENCE TIME CALCULATION

| Case | Maximum Temperature (°F.) | Residence Time (min) | Estimated PCB* Residual (ppm) |
|---|---|---|---|
| 1 | 850 | 20 | 0.13 |
| 2 | 850 | 18 | 0.37 |
| 3 | 850 | 16 | 1.03 |
| 4 | 850 | 14 | 2.90 |
| 5 | 850 | 12 | 8.17 |
| 6 | 950 | 10 | 0.14 |
| 7 | 950 | 8 | 0.45 |
| 8 | 950 | 6 | 1.43 |
| 9 | 950 | 4 | 4.57 |
| 10 | 950 | 2 | 14.54 |

*Based on equation 6 and data shown in FIG. 6.

Heat Transfer Calculation

Assumptions:

| | |
|---|---|
| To - initial temperature | 20° C. |
| k - thermal diffusivity | 0.00017 cal/cm/sec/°C. |
| Cp - heat capacity | 0.312 cal/gm/°C. |
| d - density | 1.4 gm/cm$^3$ |
| x - depth in soil | 1.27 cm |
| Fo - thermal radiation | 0.73 cal/sec/cm$^2$ |
| rod diameter - | 2.12 inches |
| rod heated length - | 95 inches |
| number of rods - | 54 |
| belt length - | 52 feet |
| belt width - | 6.8 feet |

The operating parameters, which satisfied the final PCB criteria of <5 ppm are summarized in Table 3. Capacity calculations for each of these parameters are shown in Table 4.

TABLE 3

OPERATING PARAMETERS BOUNDS

| Case | Maximum Temperature (°F.) | Residence Time (min) | Calculated Maximum Temperature** (°F.) | Total Time (sec) | Heat-Up Time (sec) |
|---|---|---|---|---|---|
| 1 | 850 | 20 | 846 | 2480 | 1280 |
| 2 | 850 | 18 | 846 | 2360 | 1280 |
| 3 | 850 | 16 | 846 | 2240 | 1280 |
| 4 | 850 | 14 | 846 | 2120 | 1280 |
| 6 | 950 | 10 | 942 | 1950 | 1350 |
| 7 | 950 | 8 | 942 | 1830 | 1350 |
| 8 | 950 | 6 | 942 | 1710 | 1350 |

**From Equation 1, using no soil turnover, 1.27 cm depth

TABLE 4

CAPACITY CALCULATION

Assumptions:

| | |
|---|---|
| d - density | 1.4 gm/cm$^3$ |
| x - soil depth on belt | 1.27 cm |
| Belt length | 1585 cm |
| Belt width | 207 cm |

| Case | Maximum Temperature (°F) | Residence Time (min) | Total Time (sec) | Belt Turnovers (/hr) | Soil Treated (lb/hr) |
|---|---|---|---|---|---|
| 1 | 850 | 20 | 2480 | 1.45 | 1870 |
| 2 | 850 | 18 | 2360 | 1.53 | 1960 |
| 3 | 850 | 16 | 2240 | 1.61 | 2070 |
| 4 | 850 | 14 | 2120 | 1.70 | 2190 |
| 6 | 950 | 10 | 1950 | 1.85 | 2380 |
| 7 | 950 | 8 | 1830 | 1.97 | 2630 |
| 8 | 950 | 6 | 1710 | 2.11 | 2710 |

Several combinations of maximum temperature and residence time may be examined to determine the optimum mode of operation. Referring to Table 4, these results indicate that higher maximum temperatures with shorter residence time at the maximum temperature provide a higher throughput than do lower maximum temperatures with longer residence times at the maximum temperature. These results indicate that the pilot unit can achieve about 1.3 tons/hr of damp soil. These results have been shown to be valid for the actual pilot unit.

Therefore, the invention provides an apparatus and method for determining the operating parameters for a thermal desorption process to remove the contaminants from the contaminated soil.

I claim:

1. Method for determining operating parameters for a thermal desorption process which removes contaminants from contaminated soil, comprising the steps of:
   obtaining a representative contaminated soil sample from a site containing the contaminated soil;
   measuring a temperature of the soil sample at a particular depth of the soil sample as a function of residence time by passing at least a portion of the soil sample through a bench scale thermal desorption process to obtain temperature, residence time and depth data;
   determining a thermal conductivity for the soil sample by using the temperature, the residence time, and the depth data obtained through the bench scale thermal desorption process; and
   determining a temperature and residence time required for removal of a particular contaminant positioned at a particular depth during a full-scale thermal desorption process using the thermal conductivity of the soil sample.

2. The method of claim 1, further comprising the step of measuring contaminant level of the soil sample after the bench scale process for determining maximum temperature and residence time required to substantially remove the contaminants from the soil.

3. The method of claim 1, further comprising the step of analyzing the soil sample prior to the bench scale process to identify particular contaminants contained within the soil sample.

4. The method of claim 1, further comprising the step of determining an absorptivity using the temperature and the depth data obtained during the bench scale process.

5. The method of claim 4, further comprising the step of determining a heating capacity of a full scale thermal desorption unit as a function of the absorptivity and thermal conductivity of the soil.

6. The method of claim 1, further comprising the step of determining a heat flux as a function of the temperature and the residence time.

7. The method of claim 6, further comprising the step of determining an absorptivity using the heat flux.

8. The method of claim 6, further comprising the step of determining a thermal diffusivity by using the heat flux and the temperature, as a function of residence time.

9. The method of claim 8, wherein the step of determining the thermal conductivity further comprises the step of using the thermal diffusivity.

10. The method of claim 1, further comprising the step of determining a thermal diffusivity by using the change in temperature with time data.

11. The method of claim 10, wherein the step of determining the thermal conductivity further comprises the step of using the thermal diffusivity.

12. The method of claim 1, further comprising the steps of:
   placing the soil sample within a container; and
   placing the container within a furnace for heating the soil sample to a temperature effective for volatilizing the contaminants and for producing a processed material that is substantially decontaminated.

13. The method of claim 12, further comprising the step of passing a transport gas through the container above the soil sample for carrying volatilized contaminants from the container.

14. The method of claim 12, further comprising the step of placing a partition between adjacent layers of the soil sample for demarcating each layer of soil.

15. The method of claim 14, further comprising the step of positioning a thermocouple within each layer of the soil sample for measuring the temperature of the soil sample at particular depths within the soil sample.

16. Method for determining operating parameters for a thermal desorption process which removes contaminants from contaminated soil, comprising the steps of:
   obtaining a representative contaminated soil sample from a site containing the contaminated soil;
   analyzing the soil sample to identify particular contaminants contained within the soil sample;
   measuring a temperature at a particular residence time for a particular depth of the soil sample by passing at least a portion of the soil sample through a bench scale thermal desorption process to obtain temperature, residence time and depth data, the bench scale thermal desorption process including the step of heating the soil sample to a temperature effective for volatilizing the contaminants and for producing a processed material that is substantially decontaminated;
   measuring contaminant level of the soil sample after the bench scale process for determining a temperature and residence time at a given depth required to substantially remove the contaminants from the soil sample;
   determining an absorptivity using the temperature and residence time data obtained from the bench scale process;
   determining a thermal diffusivity using the temperature and residence time data;
   determining a thermal conductivity for the soil sample using the thermal diffusivity; and
   determining the operating parameters of temperature and residence time of a particular contaminant at a particular depth for a full scale thermal desorption process using the thermal conductivity and absorptivity of the soil sample.

17. Method for operating a thermal desorption process, comprising the steps of:
   performing a bench scale thermal desorption process to obtain operating parameters of a full scale thermal desorption process, including the steps of:
   placing a representative contaminated soil sample from a site containing contaminated soil into a container;
   placing the container housing the soil sample into a furnace for heating the soil sample to a temperature effective for volatilizing the contaminants and for producing a processed material that is substantially decontaminated;
   measuring a temperature of the soil sample at a particular depth of the soil sample as a function of residence time as the soil sample is heated within the furnace to obtain temperature, residence time and depth data;
   measuring the contaminant level of the soil sample after volatilization of the contaminants for determining a temperature and residence time at a given depth required to substantially remove the contaminants from the soil sample;
   determining a temperature and residence time required for removal of a particular contaminant positioned at a particular depth during the full scale thermal desorption process using the data obtained during the bench scale process; and
   performing the full scale thermal desorption process, including the step of heating the contaminated soil to the temperature obtained from the bench scale process for the residence time obtained from the bench scale process for volatilizing the contaminants from the contaminated soil and for producing a processed material that is substantially decontaminated.

18. The method according to claim 17, wherein the step of performing the full scale thermal desorption process further includes the step of moving the contaminated soil positioned on a belt conveyor through a thermal desorption unit.

19. The method according to claim 17, wherein the step of performing the full scale thermal desorption process further includes the step of condensing at least a portion of the volatilized contaminants discharged from the thermal desorption unit.

20. The method according to claim 17, wherein the step of performing the full scale thermal desorption process further includes the step of passing a transport gas above the contaminated soil for carrying volatilized contaminants from the thermal desorption process.

* * * * *